(12) United States Patent
Shimizu et al.

(10) Patent No.: US 6,592,154 B2
(45) Date of Patent: Jul. 15, 2003

(54) METAL-PIPE BONDED BODY, PIPE EXPANSION METHOD OF METAL-PIPE BONDED BODY, AND METHOD FOR INSPECTING METAL-PIPE BONDED BODY

(75) Inventors: Takao Shimizu, Nagoya (JP);
Hirotsugu Horio, Nagoya (JP);
Kazushige Kito, Nagoya (JP);
Shigeyuki Inagaki, Nagoya (JP);
Ryuzo Yamada, Nagoya (JP)

(73) Assignee: Daido Tokushuko Kabushiki Kaisha (JP)

( * ) Notice: Subject to any disclaimer, the term of this patent is extended or adjusted under 35 U.S.C. 154(b) by 0 days.

(21) Appl. No.: 09/858,588

(22) Filed: May 17, 2001

(65) Prior Publication Data

US 2002/0014514 A1 Feb. 7, 2002

(30) Foreign Application Priority Data

May 30, 2000 (JP) ........................ 2000-160167
May 18, 2000 (JP) ........................ 2000-146903

(51) Int. Cl.⁷ .............................................. F16L 13/04
(52) U.S. Cl. ................... 285/332.1; 285/332; 138/109
(58) Field of Search ................. 428/609; 228/104, 228/103, 1.1, 193; 138/155, 109; 285/332, 332.1, 422, 330

(56) References Cited

U.S. PATENT DOCUMENTS 3,427,707 A * 2/1969 Nowosadko ................ 228/154
3,766,633 A * 10/1973 Lehrheuer et al .......... 228/135
5,699,955 A * 12/1997 Shimizu et al. ............. 148/526
5,831,252 A * 11/1998 Shimizu .................. 219/117.1
6,405,761 B1 * 6/2002 Shimizu et al. ............. 138/109

FOREIGN PATENT DOCUMENTS

| DE | 19513604 A1 | * | 10/1996 |
| JP | 63-005887 | * | 1/1988 |
| JP | 7-507610 | | 8/1995 |
| JP | 08-118042 | * | 5/1996 |
| JP | 09-317959 | * | 12/1997 |
| JP | 2000-107870 | * | 4/2000 |
| WO | WO 97/01057 | * | 1/1997 |
| WO | WO 98/00626 | | 1/1998 |

* cited by examiner

Primary Examiner—John J. Zimmerman
(74) Attorney, Agent, or Firm—Bacon & Thomas, PLLC

(57) ABSTRACT

In diffusion bonding a metal pipe 112e and a metal pipe 114e via a bonded interface 116e formed at the end parts, a portion that is inclined with respect to the radial direction of metal pipes 112e and 114e is provided at least at part of bonded interface 116. In this case, the inclination angle $\phi$ of bonded interface 116e and the tip angle $2\theta$ of a pipe expansion tool 130 are preferably in the relationship, $0<\phi \leq \theta+60°$. In performing pipe expansion of such a metal pipe bonded body 110e, the pipe expansion tool 130 is moved from the metal pipe 112e, at which the inclined portion of junction face 116e is formed to have a protruding shape, towards the metal pipe 114e, at which the inclined portion of junction face 116e is formed to have a recessed shape. Furthermore, the inner diameter at the vicinity of the junction face of the metal pipe junction may be made larger than the inner diameter at positions away from the junction face.

5 Claims, 6 Drawing Sheets

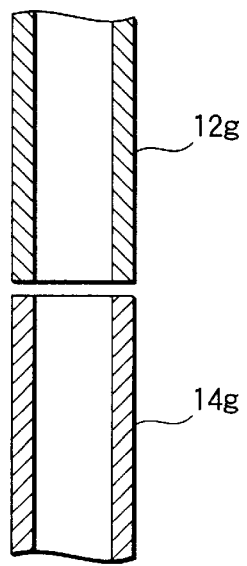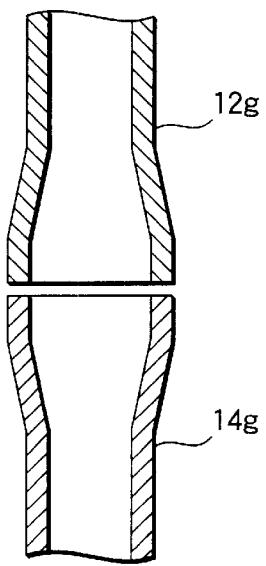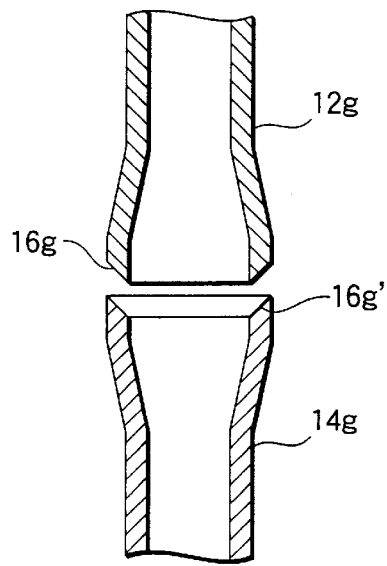

METAL-PIPE BONDED BODY, PIPE EXPANSION METHOD OF METAL-PIPE BONDED BODY, AND METHOD FOR INSPECTING METAL-PIPE BONDED BODY

BACKGROUND OF THE INVENTION

The present invention relates to a metal-pipe bonded body and a pipe expansion method of metal-pipe bonded body, and to more particularly relates to an expandable metal-pipe bonded body and a pipe expansion method of metal-pipe bonded body that are favorable for plant piping and line pipes used in the chemical industry, petrochemical industry, etc., and for casing tubes, production tubes, coiled tubes, and other oil well pipes used in oil wells.

In addition to this, the present invention also relates to a metal pipe bonded body inspection method, and more particularly relates to a metal pipe bonded body inspection method that is favorable as a nondestructive inspection method for a metal pipe bonded body having a inclined part at the bonded interface and is liquid phase diffusion bonded.

Since in the fields of chemical industry, petrochemical industry, etc., long-size metal pipes have been conventionally used for obtaining the targeted products by use of chemical reactions under various environments and for transporting the chemical reaction raw materials, intermediate products, targeted products, and other corrosive fluids over a long distance.

Though seamless steel pipes, which are excellent in corrosion resistance, are generally used as metal pipes that are exposed to corrosive environments, industrially mass-produced seamless steel pipes are 10 to 15 m in length and the upper limit for production is approximately 100 m. Thus in such cases, bonded bodies (referred to hereinafter as "metal pipe bonded bodies"), with which a plurality of seamless steel pipes of 10 to 15 m length are joined, are used.

Conventional methods for joining metal pipes include the screw connecting method (mechanical coupling method), welding methods (orbital welding method), friction welding method, diffusion bonding method, etc. Among these, the diffusion bonding method provides the advantages that a joint, which is high in air-tightness and is of a bonding strength that is equivalent to the base material strength, can be obtained and the working time is short in comparison to the welding method. The diffusion bonding method is therefore anticipated for application as a method for joining oil well pipes, line pipes, etc.

Also, though a metal pipe bonded body is generally used as it is in the joined condition, depending on the application, the process of expanding the inner diameter of the metal pipe bonded body (this process shall be referred to hereinafter as "pipe expansion") is carried out after the joining process in some cases. For example, recently in the field of oil well pipes, a method of performing pipe expansion after the burying of a metal pipe bonded body underground has been proposed for reducing the drilling cost of oil wells.

For example, a method of burying a casing, made of malleable material, in a bore hole drilled into the ground and expanding a hydraulic expanding tool inside the interior of the casing to expand the casing in the radial direction with respect to the bore hole wall has been disclosed in Japanese Patent Publication No. 507610 of 1995.

Also, International Patent Publication No. WO 98/00626, based on the Patent Cooperation Treaty, discloses a method of inserting a steel pipe, which is made of a malleable type of steel that undergoes strain hardening without undergoing necking or ductile breaking, inside a gallery or a previously buried casing, and pipe expanding the casing using a mandrel, made of nonmetallic material and having a tapered surface.

In applications of pipe expansion of a metal pipe bonded body to oil well pipes, the rate of expansion of the inner diameter before and after pipe expansion (shall be referred to hereinafter as the "pipe expansion rate") must be at least 5% and is more preferably 20% or more for reducing the drilling costs of oil wells. On the other hand, the diffusion bonding method is, as has been mentioned above, a joining method that enables the production of high-quality metal pipe bonded bodies at high efficiency. Significant reductions in oil well drilling costs can thus be anticipated by combining the diffusion bonding method with pipe expansion and applying this to oil well pipes.

However, generally in the diffusion bonding of metal pipes, butt joining is performed upon forming the bonded interface by processing the end faces of the metal pipes to be perpendicular to the axial direction. Thus when pipe expansion is performed on such a metal pipe bonded body as it is, the shearing force that acts on the bonded interface during pipe expansion increases in accompaniment with the increase of the pipe expansion rate and this can lead to the formation of cracks at the bonded interface.

Conventionally, as a bonding method for a plurality of metal pipes that constitute a metal pipe bonded body, a liquid phase diffusion bonding method is known. Due to being lower in heat deformation than the welding method and enabling a joint of the same quality as the base material to be obtained in a short time, the liquid phase diffusion bonding method is used as the method for joining such metal pipes as plant piping, line pipes, oil well pipes, etc. However, the quality of a bonded body made by the liquid phase diffusion bonding method depends sensitively on the unavoidable variations of the bonding conditions, the expertise of the worker, etc. and flaws can occur at the bonded interface. Thus when metal pipes are joined by the liquid phase diffusion bonding method, the existence of flaws at the bonded interface must be inspected in a nondestructive manner in order to assure the quality of the metal pipe bonded body that is obtained.

The X-ray transmission test method or the ultrasonic flaw detection test method, etc. is generally used as a nondestructive inspection method for a bonded body. Among these, the X-ray transmission test method is good for the inspection of three-dimensional flaws, such as blow holes, etc. Meanwhile, the ultrasonic flaw detection test method is good for the inspection of planar flaws, such as cracks, etc. In the case of the liquid phase diffusion bonding method, since the flaws that occur at the bonded interface are normally planar flaws, such as cracks, bonding faults, etc., the ultrasonic flaw detection method is used for inspection of a metal pipe bonded body made by liquid phase diffusion bonding.

Also, generally when metal pipes are liquid phase diffusion bonded, the end parts of the metal pipes are processed to be perpendicular to the axial direction and butt joining is performed. Thus in the detection of the existence of a flaw at the bonded interface, the oblique flaw detection method is generally employed in which the ultrasonic wave is made incident obliquely on the bonded interface and the existence of a flaw is judged from the magnitude of the reflected wave.

However, the conventional oblique flaw detection method is limited in terms of high-precision quantitative inspection of the magnitudes, positions, and shapes of the flaws that occur at the bonded interface.

Also, the quality of a metal pipe bonded body is not only affected by the poor fusing that occurs at the bonded interface but is also affected by the offset that is formed at the end part of the bonded interface, the crystalline structure in the vicinity of the joined parts, etc. Also, molten insert material may leak out from the bonded interface and since the resulting solidified parts are brittle, they tend to be starting points for the concentration of stress. Therefore such solidified parts must also be inspected in a nondestructive manner in order to assure the quality of the metal pipe bonded body.

SUMMARY OF THE INVENTION

It is an object that this invention attempts to achieve is to provide a metal-pipe bonded body, with which the possibility of crack formation at the bonded interface is low even when pipe expansion of a high pipe expansion rate is carried out. It is another object of the present invention to provide a pipe expansion method of metal-pipe bonded body, which enables pipe expansion of a high pipe expansion rate to be performed without causing cracks to form at the bonded interface.

The object can be achieved by a metal-pipe bonded body, according to the present invention, having a plurality of metal pipes which are diffusion bonded via a bonded interface formed at the end parts thereof. In the metal-pipe bonded body, at least part of the bonded interface is inclined with respect to the radial direction of the metal pipes.

Since with the metal-pipe bonded body of this invention, at least part of the diffusion bonded bonded interface is inclined with respect to the radial direction of the metal pipes, the shearing force that is generated at the bonded interface in the process of pipe expansion can be alleviated by moving a pipe expanding tool from one metal pipe, with which the inclined part of the bonded interface is formed to have a protruding shape, towards another metal pipe, with which the inclined part of the bonded interface is formed to have a recessed shape. Pipe expansion of the metal pipe bonded body can thus be performed without the formation of cracks at the bonded interface.

It is a further object of the present invention to provide a metal pipe bonded body inspection method by which flaws, which have occurred at the bonded interface of a metal pipe bonded body, can be detected at high precision. It is another object of the present invention to provide a metal pipe bonded body inspection method by which the magnitude of the offset that has formed at the end part of the bonded interface, the appropriateness of the crystalline structure in the vicinity of the bonded interface, and the existence of insert material that has leaked out and solidified at the end part of the bonded interface can be inspected.

In order to achieve the above objects, this invention provides in a metal pipe bonded body inspection method for inspecting, by the ultrasonic flaw detection method, a metal pipe bonded body at which a plurality of metal pipes are joined by liquid phase diffusion bonding, a metal pipe bonded body inspection method being characterized in that the bonded interface of the metal pipe bonded body has a inclined part and in having a first flaw detection process, in which an ultrasonic wave is made incident perpendicularly on the inclined part and the reflection echo that is reflected from the inclined part is detected.

Since the method of making an ultrasonic wave perpendicularly incident on the inclined part and detecting the reflection echo is employed in the metal pipe bonded body inspection method of this invention, the maximum sensitivity can be obtained. Also, by focusing the ultrasonic wave and scanning in the circumferential direction or longitudinal direction, the flaw information on the inclined part can be obtained as 2-dimensional information, and the magnitudes, positions, shapes, etc. of flaws can be obtained from this flaw information.

Also in the case where the bonded interface has a perpendicular part, the inspection method preferably has furthermore a second flaw detection process, in which an ultrasonic wave is made obliquely incident on the perpendicular part and the reflection echo that is reflected from the perpendicular part is detected. The existence of flaws at the perpendicular parts of the bonded interface may thereby be inspected.

The inspection method may also have furthermore a first pipe thickness measurement process, in which an ultrasonic wave is made perpendicularly incident on one of the metal pipes that are disposed adjacent each other across the bonded interface and the pipe thickness of the one of the metal pipes is measured from the difference in the arrival times of the surface echo and the bottom face echo, a second pipe thickness measurement process, in which an ultrasonic wave is made perpendicularly incident on the other of the metal pipes that are disposed adjacent each other across the bonded interface and the pipe thickness of the other of the metal pipes is measured from the difference in the arrival times of the surface echo and the bottom face echo, a surface offset measurement process, in which the surface offset between the one of the metal pipes and the other of the metal pipes is measured, and an inner face offset calculation process, in which the inner face offset between the one of the metal pipes and the other of the metal pipes is determined from the pipe thickness and the surface offset of the one of the metal pipes and the other of the metal pipes. The inner face offset of the metal pipe bonded body can thereby be measured in a non-destructive manner.

Also, the inspection method may furthermore have a backward scattering intensity measurement process, in which an ultrasonic wave is transmitted in the direction of the interior of the metal pipe at the vicinity of the bonded interface and the backward scattering intensity is measured, and a crystal grain diameter calculation process, in which a previously determined correlation between the crystal grain diameter of the metal pipe and the backward scattering intensity is used to determine the size of the crystal grain from the magnitude of the backward scattering intensity that was measured in the backward scattering intensity measurement process. The crystalline structure in the vicinity of the bonded body can thereby be judged.

The inspection method may furthermore have a solidified phase detection process, in which an ultrasonic wave is made obliquely incident towards the inner face end part of the metal pipe bonded body and the position of the reflection echo that is reflected from the inner face of the metal pipe bonded body is measured. The existence of a solidified phase at the inner face end part can thereby be inspected in a non-destructive manner.

BRIEF DESCRIPTION OF THE DRAWINGS

FIG. 4 is a process diagram, which illustrates an example of the method of producing a metal pipe bonded body of the second embodiment of this invention;

DETAILED DESCRIPTION OF THE PREFERRED EMBODIMENTS

Embodiments of this invention shall now be described in detail. The expandable metal-pipe bonded body of the first embodiment of this invention is one with which a plurality of metal pipes are diffusion bonded via a bonded interface formed at the end parts thereof and is characterized in that at least part of the bonded body bonded interface is inclined with respect to the radial direction of the metal pipes.

Figure 1A:
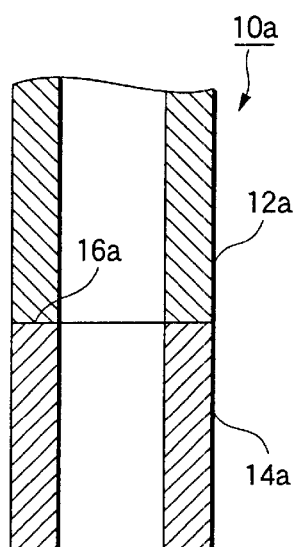
FIG. 1(a) is a sectional view of the vicinity of the bonded interface of a prior-art metal pipe bonded body and FIGS. 1(b) to 1(f) are sectional views of the vicinities of the bonded interfaces of metal pipe bonded bodies of the first embodiment of this invention.

FIG. 1(a) is a sectional view of a prior-art metal pipe bonded body. Each of FIGS. 1(b) to 1(f) shows an example of a sectional view of a metal pipe bonded body of the present embodiment. As shown in FIG. 1(a), with the prior-art metal pipe bonded body 10a, metal pipes 12a and 14a are joined at their end faces and the bonded interface 16a is perpendicular to the axial direction of metal pipes 12a and 14a.

Figure 1B:
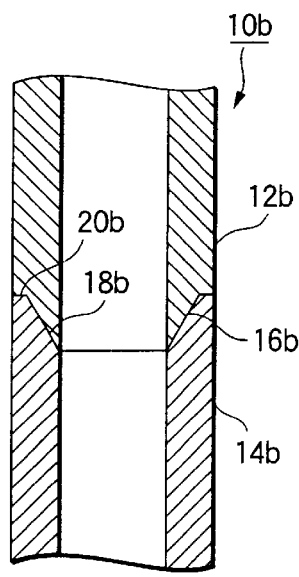

Meanwhile, with the metal pipe bonded body 10b shown in FIG. 1(b), metal pipes 12b and 14b are joined at their end faces, and bonded interface 16b is comprised of a tapered part 18b, which is inclined with respect to the radial direction of metal pipes 12b and 14b, and a first flat part 20b, which is formed at the outer peripheral sides of metal pipes 12b and 14b.

Figure 1C:
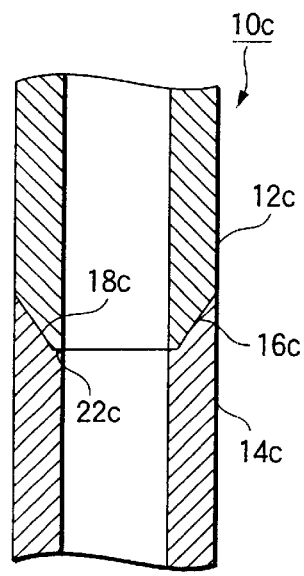

Also, with the metal pipe bonded body 10c shown in FIG. 1(c), metal pipes 12c and 14c are joined at their end faces, and bonded interface 16c is comprised of a tapered part 18c, which is inclined with respect to the radial direction of metal pipes 12c and 14c, and a second flat part 22c, which is formed at the inner peripheral sides of metal pipes 12c and 14c.

Figure 1D:
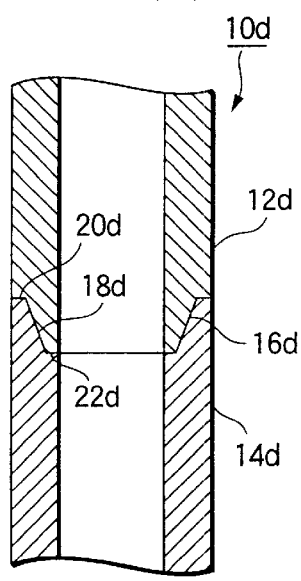

With the metal pipe bonded body 10d shown in FIG. 1(d), metal pipes 12d and 14d are joined at their end faces, and bonded interface 16d is comprised of a tapered part 18d, which is inclined with respect to the radial direction of metal pipes 12d and 14d, and a first flat part 20d and a second flat part 22d, which are formed at the outer peripheral sides and inner peripheral sides, respectively, of metal pipes 12d and 14d.

Figure 1E:
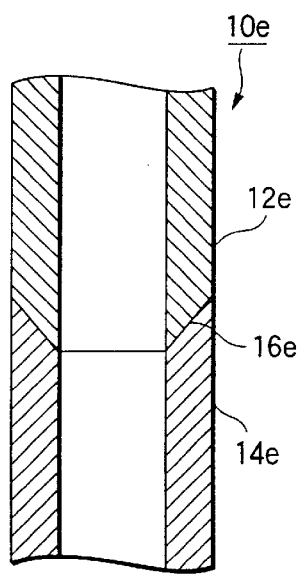

With the metal pipe bonded body 10e shown in FIG. 1(e), metal pipes 12e and 14e are joined at their end faces, and bonded interface 16e is comprised only of a tapered part, which is inclined with respect to the radial direction of metal pipes 12e and 14e.

Figure 1F:
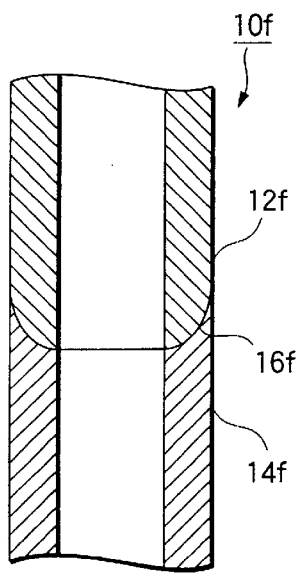

Furthermore, with the metal pipe bonded body 10f shown in FIG. 1(f), metal pipes 12f and 14f are joined at their end faces, and bonded interface 16f is comprised of a curved surface part, with which the angle of the portion that is inclined with respect to the radial direction of metal pipes 12f and 14f varies in a continuous manner.

The angle (φ) of the tapered part with respect to the radial direction of the metal pipes (referred to hereinafter as the "inclination angle") must be at least greater than 0. Though the formation of cracks at the bonded interface will be less likely the greater this inclination angle φ, processing will be made difficult if the inclination angle φ is too great. Thus if the tip angle of a pipe expansion tool is 2θ, the inclination angle φ is preferably in the range expressed by the following Formula 1.

$$0 < \phi \leq \theta + 60°$$ [Formula 1]

In the case where the portion of the bonded interface that is inclined with respect to the radial direction of the metal pipes is a curved surface part as shown in FIG. 1(f), the "inclination angle (φ)" refers to the value approximated by the angle formed by the plane formed by joining both ends of the curved surface part with a straight line and the radial direction of the metal pipes.

Diffusion bonding methods include the solid phase diffusion bonding method, with which the elements are made to undergo diffusion while maintaining the solid phase condition, and the liquid phase diffusion bonding method, with which an insert material is inserted in the bonded body interface and the insert material is melted and a part of the components thereof are made to undergo diffusion into the metal pipe side. The metal pipe bonded body by this invention may be made by either of these methods.

Figure 2A:
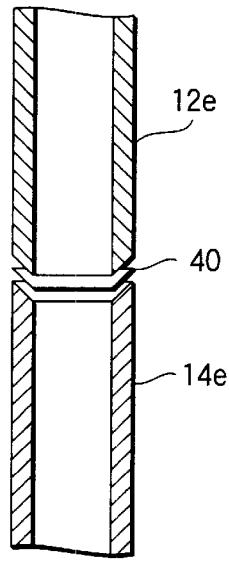
FIG. 2 is a process diagram, which illustrates an example of the method of producing a metal pipe bonded body of the first embodiment of this invention.

The method of producing the metal pipe bonded body of the present embodiment shall now be described. FIG. 2 is a process diagram, which illustrates an example of the method of producing the metal pipe bonded body 10e shown in FIG. 1(e). As shown in FIG. 2(a), a protruding type tapered part and a recessed type tapered part are formed at the end faces of metal pipe 12e and metal pipe 14e, respectively, and these are butt joined via an insert material 40.

Figure 2B:
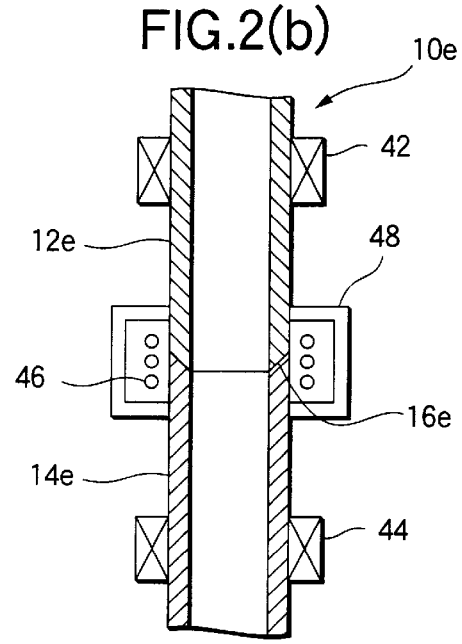

Next, as shown in FIG. 2(b), metal pipes 12e and 14e are fixed by clamps 42 and 44, respectively, and a prescribed pressure is applied to an interface to be bonded. Also, a coil 46 is positioned around the interface and the surroundings of coil 46 are sealed closely by a shield 48. Next, a high frequency current is applied to coil 46 while keeping the interior of shield 48 in a non-oxidizing atmosphere. The vicinity of the interface is then heated to the bonding temperature and after maintaining this temperature for a prescribed amount of time, cooling is performed to obtain the metal pipe bonded body 10e, with which the bonded interface 16e is comprised only of a tapered part.

A metal pipe bonded body having a flat part at part of the bonded interface or a metal pipe bonded body, with which a part of the bonded interface is a curved surface part of a prescribed radius of curvature, may also be produced by the same procedure. In the case where bonding by the solid phase diffusion bonding method is to be performed, the metal pipes are butt joined directly and heated without the insertion of insert material 40.

The actions of the metal pipe bonded body of the present embodiment shall now be described. By inserting a pipe expansion tool, with a tip angle of 2θ, into the interior of the metal pipe bonded body and moving the pipe expansion tool from one side of the metal pipe bonded body towards the other side of the metal pipe bonded body, the inner diameter of the metal pipe bonded body can be expanded uniformly by the pipe expansion tool.

However, in the process of moving the pipe expansion tool, a part of the force that acts on the pipe expansion tool acts in the radial direction of the metal pipe bonded body. Thus if the bonded interface is parallel to the radial direction of the metal pipe (that is, if the inclination angle $\phi=0$), the force that acts in the radial direction will act as it is as a shearing force on the bonded interface, and especially in the case where the pipe expansion rate is large, cracks may form in the bonded interface.

Figure 3:
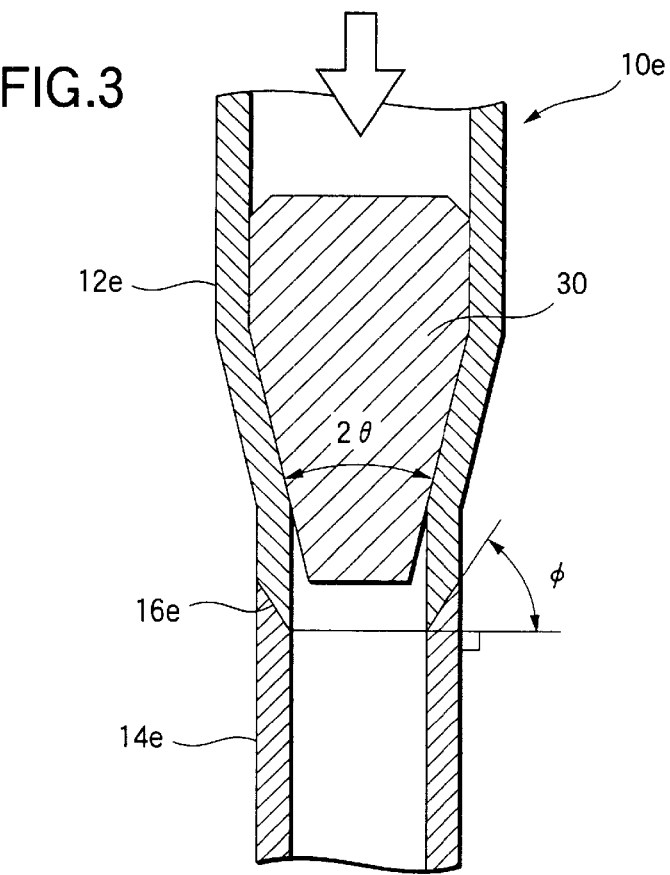
FIG. 3 is a diagram for explaining the relationship between the inclination angle φ and the tip angle 2θ.

In contrast, when for example as shown in FIG. 3, an expansion tool 30, with a tip angle of 2θ, is inserted into the interior of metal pipe bonded body 10e, with which the bonded interface 16e is comprised only of a tapered part, and the pipe expansion tool 30 is moved from the metal pipe 12e, with which the end face has a protruded shape, towards the metal pipe 14e, with which the end face has a recessed shape, only a part of the force that acts in the radial direction acts on bonded interface 16e. The shearing force that acts on bonded interface 16e in the process of pipe expansion is therefore alleviated and the formation of cracks at the bonded interface is restrained. The same applies in the case where part of the bonded interface is a flat part and in the case where part of the bonded interface is a curved surface part of a prescribed radius of curvature.

The metal pipe bonded body of a second embodiment of this invention shall now be described. The metal pipe bonded body of this embodiment is characterized in that at least part of the bonded interface is inclined with respect to the radial direction of the metal pipes and the inner diameter in the vicinity of the bonded interface is larger than the inner diameter at positions away from the bonded interface.

Here, the increase of the inner diameter in the vicinity of the bonded interface with respect to the inner diameter at positions away from the bonded interface (referred to hereinafter as the "diameter expansion rate") should be determined in accordance with the material of the metal pipes, the deformability of the vicinity of the bonded interface after joining, the tube expansion rate achieved by the tube expansion tool, etc. Generally, the closer the diameter expansion rate is to the pipe expansion rate, the more preferable since the formation of cracks during pipe expansion can then be restrained.

FIG. 4 is a process diagram, which illustrates an example of a method of producing the metal pipe bonded body of the present embodiment. As shown in FIG. 4(a), metal pipes 12g and 14g of uniform inner diameter are prepared. Then using an appropriate tool, the diameter expansion of the end parts of metal pipes 12g and 14g by a prescribed diameter expansion rate is performed using an appropriate tool as shown in FIG. 4(b).

Then as shown in FIG. 4(c), tapered parts are formed at the end faces of the diameter expanded metal pipes 12g and 14g. FIG. 4(c) shows the case where a surface (to be bonded) 16g with a protruding type tapered part is formed at the end face of metal pipe 12g and a surface (to be bonded) 16 g' with a recessed type tapered part is formed at the end face of metal pipe 14g. The metal pipes 12g and 14g thus obtained are butt joined directly or upon inserting an insert material and diffusion bonded in the same manner as the first embodiment described above to obtain a metal pipe bonded body with which the inner diameter in the vicinity of a bonded interface defined by mated surfaces 16g, 16g' is expanded.

With the metal pipe bonded body of this embodiment, since at least part of the bonded interface is inclined with respect to the radial direction of the metal pipe and since the inner diameter in the vicinity of the bonded interface is made greater than the inner diameter at positions away from the bonded interface, the force that acts in the radial direction when a pipe expansion tool passes near the bonded interface is made even smaller than in the case where diameter expansion of the end parts is not performed. The shearing force that acts on the bonded interface during pipe expansion is therefore alleviated and the formation of cracks at the bonded interface is restrained further.

EXAMPLES

Example 1

Liquid phase diffusion bonding was performed using metal pipes of different bonded interface shapes. L80 carbon steel pipes (API 5CT) of 177.8 mm outer diameter, 9.19 mm stock thickness, and 5 m length were used as the metal pipes. The shapes shown in FIGS. 1(a) to 1(e) were used as the shapes of the bonded interfaces, and liquid phase diffusion bonding was performed without performing diameter expansion of the end parts.

The bonding conditions are as follows:

| | |
|---|---|
| Insert material: | BNi-3 (t40 μm, JISZ3265) |
| Bonding temperature: | 1250° C. |
| Holding time: | 180 s |
| Compression force: | 3 MPa |
| Bonding atmosphere: | Ar |

Five (5) each of metal pipe bonded bodies of different bonded interface shapes were made under the bonding conditions given above and pipe expansion was performed on each of these metal pipe bonded bodies. For pipe expansion, a pipe expansion tool, with a tip angle 2θ of 30°, was inserted into the interior of the metal pipe bonded body and was moved using hydraulic pressure at a travel speed of 10 m/min. In all cases of the present example, the pipe expansion tool was moved from a metal pipe, with which the end face was formed to have a protruding shape, towards a metal pipe, with which the end face was formed to have a recessed shape (hereinafter, this direction of movement shall be referred to as the "up→down" direction and the opposite direction of movement shall be referred to as the "down→up" direction). Also in all cases of the present examples the pipe expansion rate was set to 20%. Dye penetrant tests were then performed on the inner and outer surfaces of the bonded body parts of the metal pipe bonded bodies on which pipe expansion was performed. Furthermore, tension tests, using a universal tester (500Tonf), were performed to evaluate the stability of the tensile characteristics. The results are shown in Table 1.

TABLE 1

| | Experiment No. | | | | |
|---|---|---|---|---|---|
| | 1 | 2 | 3 | 4 | 5 |
| Joint | | | | | |
| Shape | FIG. 1 (a) | FIG. 1 (b) | FIG. 1 (c) | FIG. 1 (d) | FIG. 1 (e) |
| $\phi$ (°) | 0 | 30 | 30 | 30 | 30 |
| Rmax (μm) | 12 | 12 | 12 | 12 | 12 |
| Pipe expansion conditions | | | | | |
| 2θ (°) | 30 | 30 | 30 | 30 | 30 |
| Pipe expansion rate (%) | 20 | 20 | 20 | 20 | 20 |

TABLE 1-continued

| | Experiment No. | | | | |
|---|---|---|---|---|---|
| | 1 | 2 | 3 | 4 | 5 |
| Tool travel speed (m/min) | 10 | 10 | 10 | 10 | 10 |
| Tool movement direction | Up → Down | Up → Down | Up → Down | Up → Down | Up → Down |
| Characteristic of the Pipe-expanded metal pipe bounded body | | | | | |
| Dye penetrant test results | | | | | |
| 1 | | | | | |
| Outer surface | Good | Good | Good | Good | Good |
| Inner surface | Good | Good | Good | Good | Good |
| 2 | | | | | |
| Outer surface | Good | Good | Good | Good | Good |
| Inner surface | Good | Good | Good | Good | Good |
| 3 | | | | | |
| Outer surface | Good | Good | Good | Good | Good |
| Inner surface | Good | Good | Good | Good | Good |
| 4 | | | | | |
| Outer surface | Good | Good | Good | Good | Good |
| Inner surface | Good | Good | Good | Good | Good |
| 5 | | | | | |
| Outer surface | Good | Good | Good | Good | Good |
| Inner surface | Microscopic cracks | Good | Good | Good | Good |
| Tension test results | | | | | |
| Tensile strength (MPa) | | | | | |
| 1 | 786 | 785 | 783 | 791 | 792 |
| 2 | 790 | 791 | 789 | 788 | 788 |
| 3 | 788 | 784 | 784 | 785 | 786 |
| 4 | 784 | 787 | 785 | 789 | 787 |
| 5 | 742 | 790 | 787 | 790 | 785 |
| Fractured Portion | | | | | |
| 1 | Base material | Base material | Base material | Base material | Base material |
| 2 | Base material | Base material | Base material | Base material | Base material |
| 3 | Base material | Base material | Base material | Base material | Base material |
| 4 | Base material | Base material | Base material | Base material | Base material |
| 5 | Junction face | Base material | Base material | Base material | Base material |
| Evaluation | Δ | ○ | ○ | ○ | ○ |

In the case of Experiment No. 1, with which the bonded interface was processed to be perpendicular with respect to the axial direction of the metal pipes as shown in FIG. 1(a), cracks in the vicinity of the bonded interface were not observed or identified in four of the five samples prepared in the dye penetrant test. These samples also exhibited tensile strengths of 780 to 790 MPa and all test pieces were fractured in the base material. However, microscopic cracks were found at the inner face side of the bonded body part of one of the five samples. This sample also was fractured at the bonded interface in the tensile test and the tensile strength was decreased to approximately 740 MPa.

On the other hand, in the cases of Experiment No. 2 to Experiment No. 5, with which a tapered part (inclination angle $\phi=30°$) was provided at least at part of the bonded interface as shown in FIGS. 1(b) to 1(e), cracks in the vicinity of the bonded interface were not observed in any of the five samples prepared. Also, tensile strength values of 780 to 790 MPa were obtained in a stable manner in all cases and all test pieces were fractured in the base material.

Example 2

Liquid phase diffusion bonding was performed using metal pipes that differed in bonded interface shapes. The same metal pipes as those of Example 1 were used and diameter expansion of the end parts by a diameter expansion rate of 10 to 20% was performed on each of these metal pipes. Then after processing the bonded interfaces to the shapes shown in FIGS. 1(b) to 1(f), liquid phase diffusion bonding was performed. The bonding conditions were the same as those of Example 1.

Five (5) each of metal pipe bonded bodies of different bonded interface shapes were made under the bonding conditions and pipe expansion were performed on each of these metal pipe bonded bodies. For pipe expansion, a pipe expansion tool, with a tip angle 2θ of 30°, was inserted into the interior of the metal pipe bonded body and was moved using hydraulic pressure at a travel speed of 10 m/min. With the present example, the pipe expansion tool was moved in the "up→down" direction. Also in all cases of the present example, the pipe expansion rate was set to 25%. Dye penetrant tests were then performed on the inner and outer surfaces of the bonded body parts of the metal pipe bonded bodies on which pipe expansion was performed. Furthermore, tension tests, using a universal tester (500Tonf) were performed to evaluate the stability of the tensile characteristics. The results are shown in Table 2.

TABLE 2

| | Experiment No. | | | | |
|---|---|---|---|---|---|
| | 6 | 7 | 8 | 9 | 10 |
| Diameter expansion rate of metal pipe end parts | 10% | 10% | 15% | 15% | 20% |
| Joint | | | | | |
| Shape | FIG. 1 (b) | FIG. 1 (c) | FIG. 1 (d) | FIG. 1 (e) | FIG. 1 (f) |
| φ (°) | 30 | 30 | 30 | 30 | 30* |
| Rmax (μm) | 12 | 12 | 12 | 12 | 12 |
| Pipe expansion conditions | | | | | |
| 2θ (°) | 30 | 30 | 30 | 30 | 30 |
| Pipe expansion rate (%) | 25 | 25 | 25 | 25 | 25 |
| Tool travel speed (m/min) | 10 | 10 | 10 | 10 | 10 |

TABLE 2-continued

| | Experiment No. | | | | |
|---|---|---|---|---|---|
| | 6 | 7 | 8 | 9 | 10 |
| Tool movement direction | Up → Down | Up → Down | Up → Down | Up → Down | Up → Down |
| Characteristic of the Pipe-expanded metal pipe bonded body | | | | | |
| Dye penetrant test results | | | | | |
| 1 | | | | | |
| Outer surface | Good | Good | Good | Good | Good |
| Inner surface | Good | Good | Good | Good | Good |
| 2 | | | | | |
| Outer surface | Good | Good | Good | Good | Good |
| Inner surface | Good | Good | Good | Good | Good |
| 3 | | | | | |
| Outer surface | Good | Good | Good | Good | Good |
| Inner surface | Good | Good | Good | Good | Good |
| 4 | | | | | |
| Outer surface | Good | Good | Good | Good | Good |
| Inner surface | Good | Good | Good | Good | Good |
| 5 | | | | | |
| Outer surface | Good | Good | Good | Good | Good |
| Inner surface | Good | Good | Good | Good | Good |
| Tension test recults | | | | | |
| Tensile strength (MPa) | | | | | |
| 1 | 813 | 811 | 816 | 814 | 811 |
| 2 | 811 | 815 | 813 | 819 | 813 |
| 3 | 809 | 820 | 811 | 810 | 816 |
| 4 | 814 | 816 | 817 | 816 | 817 |
| 5 | 810 | 814 | 815 | 813 | 814 |
| Fractured Portion | | | | | |
| 1 | Base material | Base material | Base material | Base material | Base material |
| 2 | Base material | Base material | Base material | Base material | Base material |
| 3 | Base material | Base material | Base material | Base material | Base material |
| 4 | Base material | Base material | Base material | Base material | Base material |
| 5 | Base material | Base material | Base material | Base material | Base material |
| Evaluation | ○ | ○ | ○ | ○ | ○ |

*inclination determined by planar approximation of the curved surface

With the present example, since at least part of the bonded interface was provided with a tapered part (inclination angle φ=30°) as shown in FIGS. 1(b) to 1(f), cracks were not observed in the vicinity of the bonded interface with all five samples. Also, tensile strength values of 810 to 820 MPa were obtained in a stable manner in all cases and all test pieces were fractured in the base material.

Example 3

Liquid phase diffusion bonding was performed using metal pipes of different bonded interface shapes. ASTM A106 carbon steel pipes of 139.7 mm outer diameter, 6.99 mm stock thickness, and 5 m length were used as the metal pipes. The shapes shown in FIGS. 1(b), 1(d), and 1(e) were used as the shapes of the bonded interfaces, and for the sample having the bonded interface shape of FIG. 1(b), liquid phase diffusion bonding was performed without performing diameter expansion of the end parts. With the samples having the bonded interface shape of FIG. 1(d) or FIG. 1(e), liquid phase diffusion bonding was performed upon diameter expansion of the end parts by a diameter expansion rate of 10% and subsequent finishing of the bonded interfaces to the prescribed shapes.

The bonding conditions are as follows:

| | |
|---|---|
| Insert material: | BNi-5 (t50 μm, JISZ3265) |
| Bonding temperature: | 1300° C. |
| Holding time: | 180 s |
| Compression force: | 3 MPa |
| Bonding atmosphere: | $N_2$ |

Five (5) each of metal pipe bonded bodies of different bonded interface shapes were made under the bonding conditions given above and pipe expansion were performed on each of these metal pipe bonded bodies. For pipe expansion, a pipe expansion tool, with a tip angle 2θ of 30°, was inserted into the interior of the metal pipe bonded body and was moved using hydraulic pressure at a travel speed of 10 m/min. With the present example, the pipe expansion tool was moved in the "down→up" direction only in the case of Experiment No. 15, and the pipe expansion tool was moved in the "up→down" direction for the rest of the samples. Also in all cases of the present example, the pipe expansion rate was set to 15%. Dye penetrant tests were then performed on the inner and outer surfaces of the bonded body parts of the metal pipe bonded bodies on which pipe expansion was performed. Furthermore, tension tests, using a universal tester (500Tonf), were performed to evaluate the stability of the tensile characteristics. The results are shown in Table 3.

TABLE 3

| | Experiment No. | | | | |
|---|---|---|---|---|---|
| | 11 | 12 | 13 | 14 | 15 |
| Diameter expansion rate of metal pipe end parts | Not expanded | Not expanded | 10% | 10% | 10% |
| Joint | | | | | |
| Shape | FIG. 1 (b) | FIG. 1 (b) | FIG. 1 (d) | FIG. 1 (e) | FIG. 1 (e) |
| φ (°) | 80 | 60 | 45 | 30 | 30 |
| Rmax (μm) | 12 | 12 | 12 | 12 | 12 |
| Pipe expansion conditions | | | | | |
| 2θ (°) | 30 | 30 | 30 | 30 | 30 |
| Pipe expansion rate (%) | 15 | 15 | 15 | 15 | 15 |
| Tool travel speed (m/min) | 10 | 10 | 10 | 10 | 10 |

TABLE 3-continued

| | Experiment No. | | | | |
|---|---|---|---|---|---|
| | 11 | 12 | 13 | 14 | 15 |
| Tool movement direction | Up → Down | Up → Down | Up → Down | Up → Down | Down → Up |
| Characteristic of the Pipe-expanded metal pipe bonded body | | | | | |
| Dye penetrant test results | | | | | |
| 1 | | | | | |
| Outer surface | Good | Good | Good | Good | Good |
| Inner surface | Microscopic cracks | Good | Good | Good | Good |
| 2 | | | | | |
| Outer surface | Good | Good | Good | Good | Good |
| Inner surface | Good | Good | Good | Good | Microscopic cracks |
| 3 | | | | | |
| Outer surface | Good | Good | Good | Good | Good |
| Inner surface | Good | Good | Good | Good | Good |
| 4 | | | | | |
| Outer surface | Good | Good | Good | Good | Good |
| Inner surface | Good | Good | Good | Good | Good |
| 5 | | | | | |
| Outer surface | Good | Good | Good | Good | Good |
| Inner surface | Microscopic cracks | Good | Good | Good | Good |
| Tension test results | | | | | |
| Tensile strength (MPa) | | | | | |
| 1 | 468 | 477 | 475 | 478 | 471 |
| 2 | 472 | 474 | 472 | 477 | 473 |
| 3 | 478 | 478 | 470 | 476 | 475 |
| 4 | 473 | 475 | 471 | 480 | 470 |
| 5 | 459 | 476 | 477 | 479 | 474 |
| Fractured Portion | | | | | |
| 1 | Junction face | Base material | Base material | Base material | Base material |
| 2 | Base material | Base material | Base material | Base material | Junction face |
| 3 | Base material | Base material | Base material | Base material | Base material |
| 4 | Base material | Base material | Base material | Base material | Base material |
| 5 | Junction face | Base material | Base material | Base material | Base material |
| Evaluation | Δ | ○ | ○ | ○ | Δ |

With three of the five samples prepared in Experiment No. 11, in which the bonded interface was made to have the shape shown in FIG. 1(b) and have an inclination angle of φ=80°, cracks were not found in the vicinity of the bonded interface by the dye penetrant test. These samples also exhibited a tensile strength of approximately 470 MPa and all test pieces were fractured in the base material. However, microscopic cracks were found at the inner face side of the bonded body part of two of the five samples. These samples also were fractured at the bonded interface and were found to be somewhat lowered in tensile strength in the tension test.

On the other hand, with all five samples prepared in Experiment No. 12, in which the bonded interface was made to have the shape shown in FIG. 1(b) and have an inclination angle of φ=60°, cracks were not found in the vicinity of the bonded interface. Also with all of these samples, tensile strength values of 470 to 480 MPa were obtained in a stable manner and all test pieces were fractured in the base material.

With all five samples prepared respectively in Experiment No. 13 and Experiment No. 14, in which the bonded interface was made to have the shape shown in FIG. 1(d) or FIG. 1(e) upon performing diameter expansion of the metal pipe end parts by a diameter expansion rate of 10%, cracks were not found in the vicinity of the bonded interface. Also with all of these samples, tensile strength values of 470 to 480 MPa were obtained in a stable manner and all test pieces were fractured in the base material.

Meanwhile, with four of the five samples prepared in Experiment No. 15, in which the tool was moved in the "down→up" direction, cracks were not found in the vicinity of the bonded interface by the dye penetrant test. These samples also exhibited a tensile strength of approximately 470 MPa and all test pieces were fractured in the base material. However, microscopic cracks were found at the inner face side of the junction part of one of the five samples. This sample was also fractured the bonded interface in the tension test.

Though embodiments of this invention were described in detail above, this invention is by no means limited to the above embodiments and various modifications are possible within scope that does not fall outside the gist of this invention.

For example, though examples to which this invention was applied to carbon steel pipes were described in the above description of the embodiments, the metal pipes used in this invention are not limited to carbon steel pipes and this invention can be applied to metal pipes of various materials. Also, though this invention is especially favorable for oil well pipes, the application of this invention is not limited to oil well pipes and may also be applied to line pipes and various forms of plant piping.

Hereinafter, the metal pipe junction inspection method according to the present invention shall now be described. This invention concerns a method of inspecting, by use of the ultrasonic flaw detection method, the qualities of a metal pipe bonded body made by liquid phase diffusion bonding. The qualities to be evaluated specifically include the existence of flaws at the bonded interface of a metal pipe bonded body having a inclined part and a perpendicular part, the size of the offset that has formed at the inner face end part of the bonded interface, the diameters of crystal grains in the vicinity of the bonded interface, and the existence of a solidified phase at the inner face end part of the bonded interface.

Figure 5:
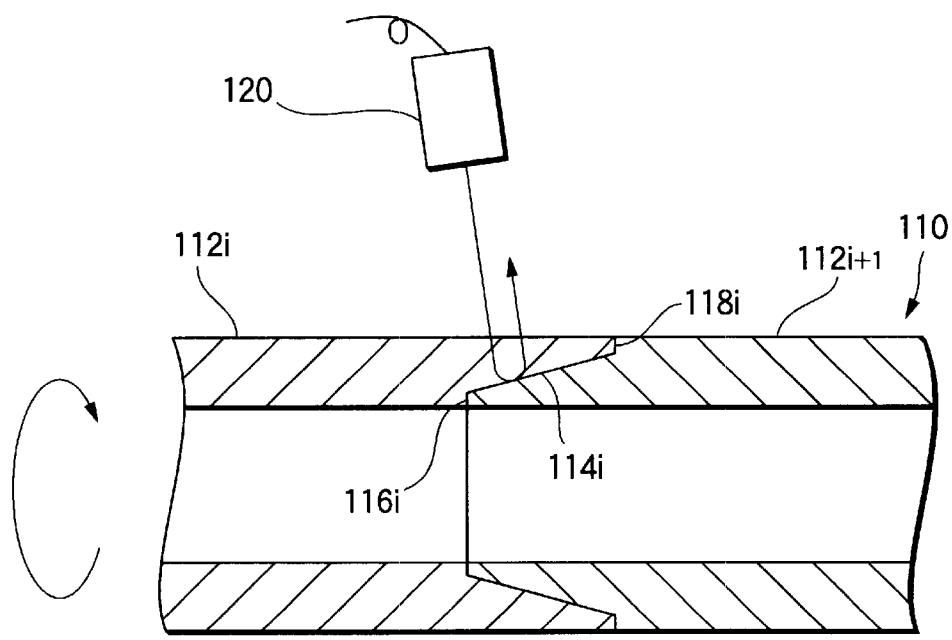
FIG. 5 is a diagram for explaining the method for inspecting for flaws that have occurred at the inclined part.

First, the process of inspecting for flaws at the inclined part of the bonded interface of a metal pipe bonded body having a inclined part and a perpendicular part (first flaw detection process) shall be described. FIG. 5 is a schematic view, which illustrates the method of detecting a flaw that has occurred at the inclined part. In FIG. 5, metal pipe bonded body 110 is made by the liquid phase diffusion bonding of a plurality of metal pipes $112_n$ (n=1, 2 - - - ) and of these pipes, two metal pipes $112_i$ and $112_{i+1}$ are shown as examples.

As shown in FIG. 5, the right end of metal pipe $112_i$ has been processed to have a recessed form and the left end of metal pipe $112_{i+1}$ has been processed to have a protruding form. Also, the bonded interface has a inclined part $114_i$ and perpendicular parts $116_i$ and $118_i$. The metal pipes $112_i$ and $112_{i+1}$ are joined by butt joining the right end of the metal pipe $112_i$ that has been processed to have a recessed form with the left end of the metal pipe $112_{i+1}$ that has been processed to have a protruding form upon interposing an insert material (not shown) in between and maintaining a temperature that is equal to or greater than the melting point of the insert material and yet less than the melting point of the metal pipes $112_i$ and $112_{i+1}$.

To detect a flaw that has occurred at inclined part $114_i$, first an ultrasonic probe 120 is positioned at a prescribed distance from metal pipe bonded body 110. Here, a focusing-type probe is preferably used as the ultrasonic probe 120. The use of a focusing-type probe enables minute flaws to be identified and provides the advantages of improved sensitivity and S/N ratio. A suitable contact medium is interposed between metal pipe bonded body 110 and ultrasonic probe 120. Normally, water is used as the contact medium. Next, an ultrasonic wave is made perpendicularly incident on inclined part $114_i$ from ultrasonic probe 120. The angle of incidence of the ultrasonic wave on metal pipe bonded body 110 should be set in consideration of the sound velocity difference between the contact medium and the metal pipes $112_i$ and $112_{i+1}$.

Here, if inclined part $114_i$ does not have a flaw, since the incident ultrasonic wave will pass right through inclined part $114_i$ and be reflected by the inner face of metal pipe bonded body 110, a reflection echo will not be detected by ultrasonic probe 120. On the other hand, if there is a flaw at inclined part $114_i$, since the reflection echo that has been reflected by the flaw will travel along substantially the same path as the incident wave and be received by ultrasonic probe 120, it can readily be known that there is a flaw at inclined part $114_i$.

Figure 6:
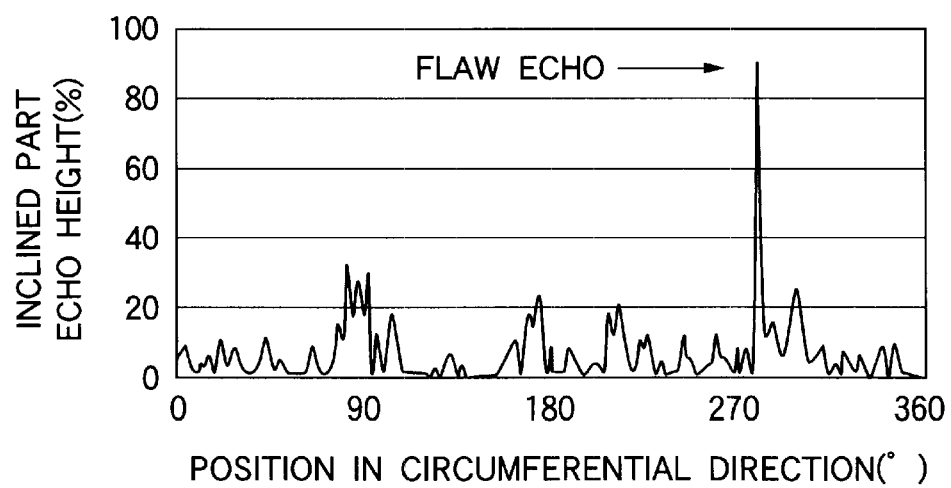
FIG. 6 is a diagram, which shows the results of inspection of the inclined part of a metal pipe bonded body using the method shown in FIG. 5.

Here, the existence of flaws at inclined part $114_i$ can be inspected across the entire circumference of metal pipe bonded body 110 by rotating metal pipe bonded body 110 in one direction. Furthermore, by scanning the ultrasonic probe 120 in the longitudinal direction of metal pipe bonded body 110 at the same time as rotating metal pipe bonded body 110 in one direction, the reflection echo can be detected as two-dimensional information, thereby enabling not only the existence of flaws to be inspected across the entire surface of inclined part $114_i$ but the sizes, positions, and shapes of the flaws to be evaluated quantitatively. An example of a result of inspecting for the existence of flaws in the circumferential direction is shown in FIG. 6. From FIG. 6, it can be understood that a flaw echo is detected at the position of approximately 270 degrees.

Figure 7:
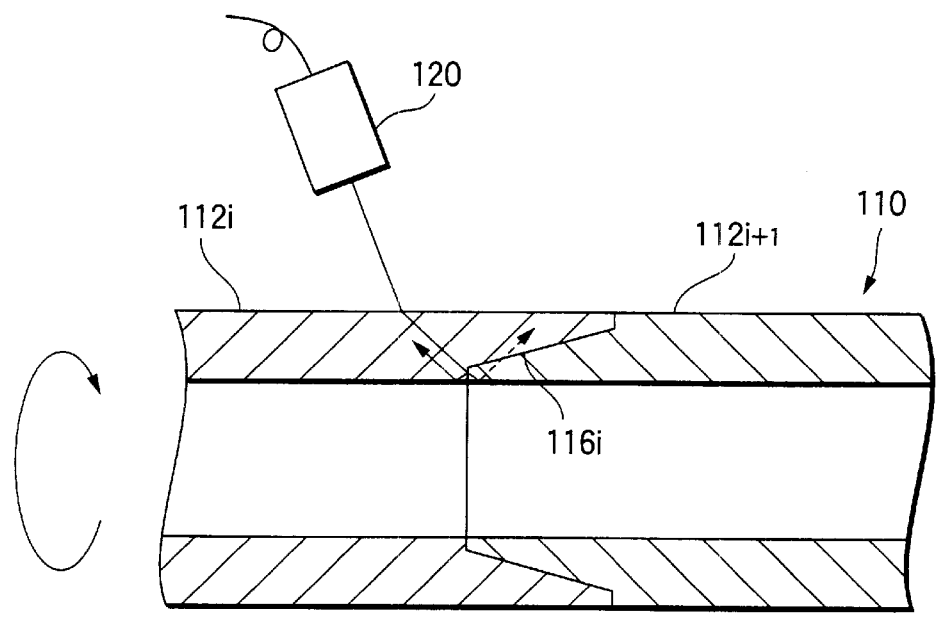
FIG. 7 is a diagram for explaining the method for inspecting for flaws that have occurred at the perpendicular part.

Next, the process of inspecting for the existence of flaws at the perpendicular part of the bonded interface of the metal pipe bonded body having a inclined part and a perpendicular part (second flaw detection process) shall be described. FIG. 7 is a schematic view, which shows the method of detecting a flaw that has occurred at the perpendicular part. To detect the existence of a flaw at perpendicular part $116_i$, first the ultrasonic probe 120 is positioned at a prescribed distance from metal pipe bonded body 110 as shown in FIG. 7 and a contact medium is interposed between metal pipe bonded body 110 and ultrasonic probe 120. Next, an ultrasonic wave is made incident obliquely towards perpendicular part $116_i$ from ultrasonic probe 120.

If perpendicular part $116_i$ does not have a flaw, since the incident ultrasonic wave will pass right through perpendicular part $116_i$ and be reflected by the inner face of metal pipe bonded body 110, a reflection echo will not be detected by ultrasonic probe 120. On the other hand, if there is a flaw at perpendicular part $116_i$, since the reflection echo that has been reflected by the flaw will travel along substantially the same path as the incident wave and be received by ultrasonic probe 120, it can readily be known that there is a flaw at perpendicular part $116_i$. Here, the existence of flaws at perpendicular part $116_i$ can be inspected across the entire circumference of metal pipe bonded body 110 by rotating metal pipe bonded body 110 in one direction.

Figure 8:
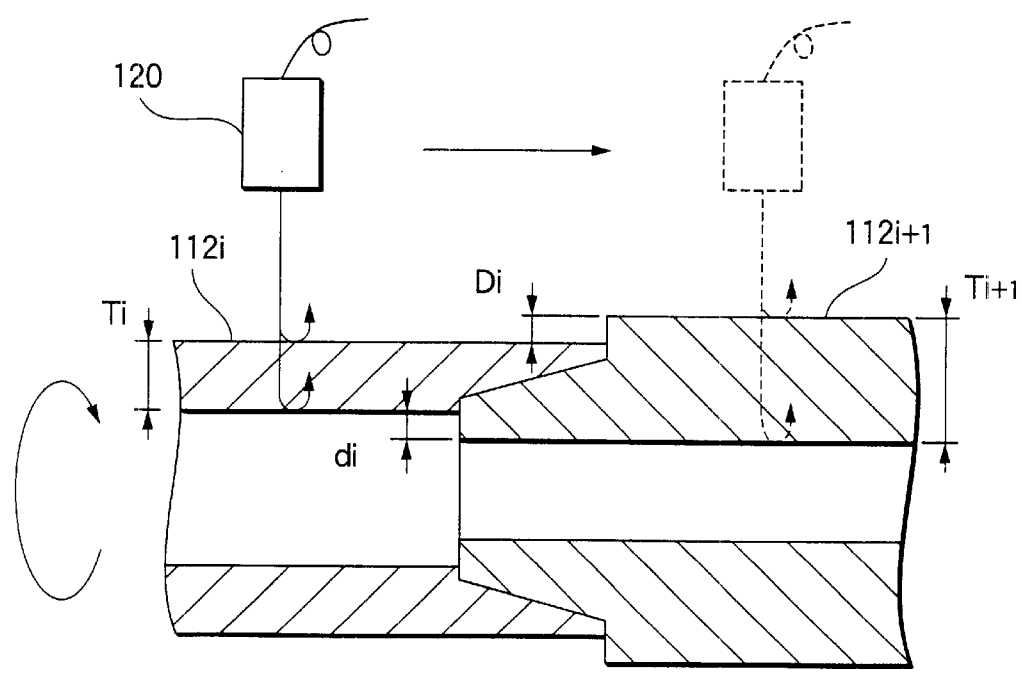
FIG. 8 is a diagram for explaining the method for measuring the inner face offset of the bonded interface.

Next, the method for measuring the magnitude of a offset that has formed at the inner face end part of the bonded interface shall be described. The offset is measured by the following procedure. First, as shown in FIG. 8, ultrasonic probe 120 is positioned at a prescribed distance from one metal pipe $112_i$ of the metal pipes that are adjacent each other across the bonded interface of metal pipe bonded body 110. At this time, a contact medium is interposed between metal pipe $112_i$ and ultrasonic probe 120. Next, an ultrasonic wave is made incident perpendicularly on metal pipe $112_i$. Since the ultrasonic wave is reflected by the surface and the inner face of metal pipe $112_i$, the pipe thickness $T_i$ of metal pipe $112_i$ can be measured from the difference in the arrival time of the surface echo and the bottom face echo (first pipe thickness measurement process) Next, ultrasonic probe 120 is moved to the metal pipe $112_{i+1}$ side, and the pipe thickness $T_{i+1}$ of metal pipe $112_{i+1}$ is measured by the same procedure that was performed for metal pipe $112_i$ (second pipe thickness measurement process).

Next, the offset $D_i$ that has formed at the surface side of the bonded interface of metal pipe $112_i$ and metal pipe $112_{i+1}$ (this offset shall be referred to hereinafter as the "surface offset") is measured (surface offset measurement process). The method for measuring the surface offset $D_i$ is not restricted in particular. For example, it may be measured using calipers, etc. Also, an ultrasonic wave may be made perpendicularly incident on metal pipe $112_i$ and metal pipe $112_{i+1}$ while keeping the positional relationship between metal pipe bonded body 110 and ultrasonic probe 120 fixed and the surface offset $D_i$ may also be determined from the difference in the arrival time of the surface echo obtained from metal pipe $112_i$ and the arrival time of the surface echo obtained from metal pipe $112_{i+1}$.

Next, using the determined pipe thickness $T_i$ of metal pipe $112_i$, pipe thickness $T_{i+1}$ of metal pipe $112_{i+1}$, and surface offset $D_i$, the offset $d_i$ that has formed on the inner face side of the bonded interface (this offset shall be referred to hereinafter as the "inner face offset") is calculated (inner face offset calculation process). For example, when as shown in FIG. 8, the surface of metal pipe $112_{i+1}$ is more protruded than the surface of metal pipe $112_i$, the inner face offset $d_i$ can be determined using the following equation.

$$d_i = T_{i+1} + (T_i + D_i)$$

Figure 9:
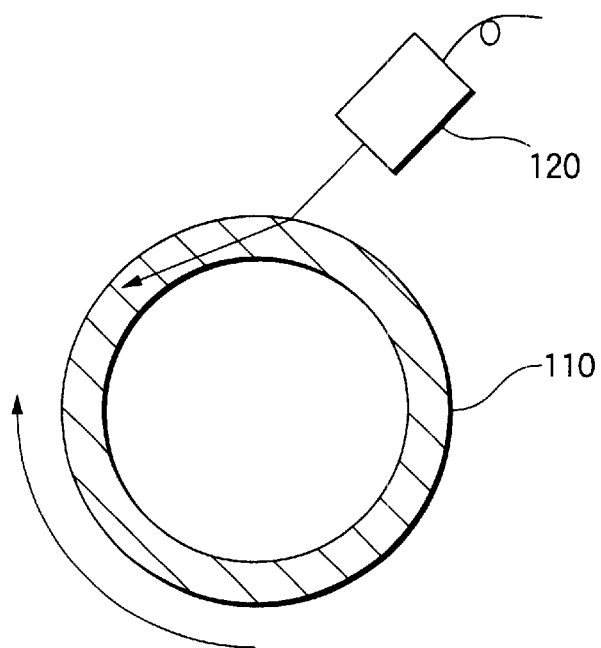
FIG. 9 is a diagram for explaining the method for judging the crystalline structure in the vicinity of the bonded interface.

Next, the method for judging the crystalline structure in the vicinity of the bonded interface shall be described The judgment of the crystalline structure is made by the following procedure. First, as shown in FIG. 9, ultrasonic probe 120 is positioned at a prescribed distance from the vicinity of the bonded body part of metal pipe bonded body 110. At this time, a contact medium is interposed between metal pipe $112_i$ and ultrasonic probe 120. Next, an ultrasonic wave is transmitted in the direction of the interior of metal pipe bonded body 110 at the vicinity of the bonded interface of metal pipe bonded body 110. Here, the "direction of the interior" refers to the direction in which a reflection echo that is reflected from the surface or the bottom face of metal pipe $112_i$ will not he observed. To be more specific, an ultrasonic wave that is made incident on metal pipe bonded body 110 is made to be transmitted in the circumferential direction, longitudial direction, or a direction intermediate these directions of metal pipe bonded body 110. FIG. 9 shows an example where an ultrasonic wave is made to be transmitted in the circumferential direction of metal pipe bonded body 110. The incidence angle of the ultrasonic wave should be determined in consideration of the sound velocity difference between the contact medium and the metal pipes $112_i$ and $112_{i+1}$.

Though the incident ultrasonic wave will be transmitted through metal pipe bonded body 110, a portion thereof will be reflected by the grain boundary, reach ultrasonic probe 120 via the same path as the incident wave, and be received by the probe as a backward scattered wave (backward scattering intensity measurement process). Since there is a correlation between the backward scattering intensity and the crystal grain diameter, the crystal grain diameter can be calculated back from the measured backward scattering intensity if this correlation has been determined in advance (crystal grain diameter calculation process).

Figure 10:
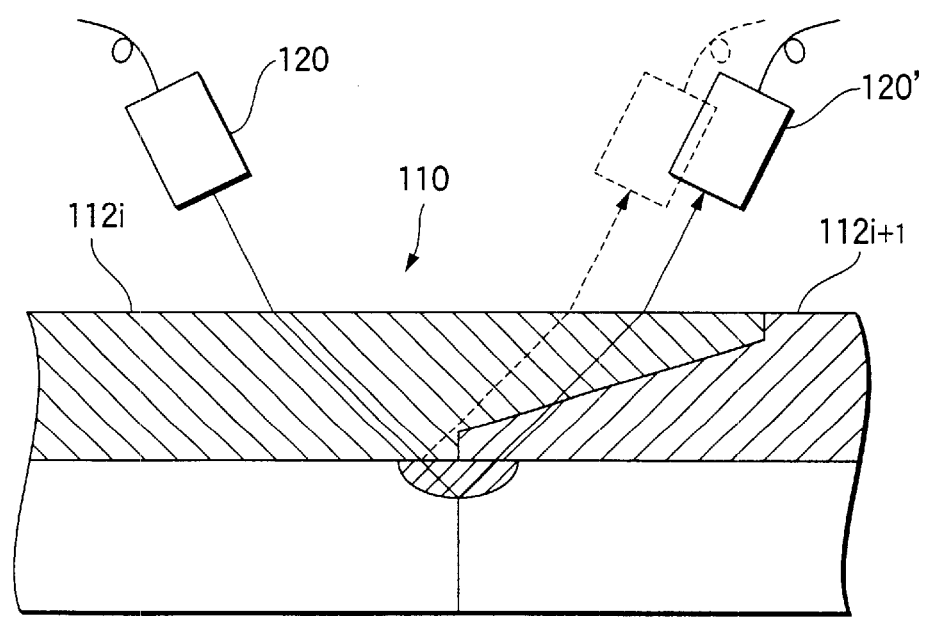
FIG. 10 is a diagram for explaining the method for detecting a solidified phase that has formed at the inner face end part of the bonded interface.

Next, the method for inspecting the existence of a solidified phase that has formed at the inner face end part of the bonded interface shall be described. The inspection for the existence of a solidified phase is performed by the following procedure. First, as shown in FIG. 10 ultrasonic probe 120 is positioned at a prescribed distance from metal pipe bonded body 110 and a contact medium is interposed between metal pipe bonded body 110 and ultrasonic probe 120. Next, an ultrasonic wave is made obliquely incident towards the inner face end part of the bonded interface from ultrasonic probe 120.

If a solidified phase does not exist at the inner face end part of the bonded interface, the incident ultrasonic wave will be reflected by the inner face of metal pipe bonded body 110 as shown by the dotted line in FIG. 10. On the other hand, if there is a solidified phase at the inner face end part of the bonded interface, the incident ultrasonic wave will reach the solidified phase upon transmission through the inner face of metal pipe bonded body 110 and be reflected by the surface of the solidified phase as shown by the solid line in FIG. 10. The position of arrival of the reflected wave will therefore vary depending on the existence of a solidified phase. By measuring this variation of the arrival position by means of another ultrasonic probe 120', the existence of a solidified phase at the inner face end part of the bonded interface can be judged readily.

Though embodiments of this invention have been described in detail above, this invention is by no means limited to the above-described embodiments and various modifications are possible within a scope that will not fall outside the gist of this invention. For example, though in all of the above-described embodiments, the various inspections are performed without bringing the ultrasonic probe in close contact with the metal pipe bonded body, the inspections may also be performed upon bringing the ultrasonic probe in close contact with the metal pipe bonded body.

Also though methods with which various inspections are performed using one ultrasonic probe or one pair of ultrasonic probes were described with the embodiments above, two or more ultrasonic probes or two or more pairs of ultrasonic probes may be used to carry out one type of inspection. Also, two or more ultrasonic probes or two or more pairs of ultrasonic probes may be used to carry out two or more types of inspection at the same time.

Note that although in the above-mentioned description, the preferred embodiments of a metal-pipe bonded body, a pipe expansion method of metal-pipe bonded body and a method for inspecting metal-pipe bonded body, according to the present invention are separately explained, it is possible for a person skilled in the art to combine these embodiments and utilize the same simultaneous in accordance with needs.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

Since the metal-pipe bonded body by this invention is a bonded body made by diffusion bonding a plurality of metal pipes via a bonded interface formed at the end parts of the pipes and at least part of the bonded interface is inclined with respect to the radial direction of the metal pipes, the effect that the formation of cracks at the bonded interface is restrained is provided even in the case where pipe expansion of a high pipe expansion rate is performed.

In the case where the inner diameter at the vicinity of the bonded interface is made greater than the inner diameter at positions away from the bonded interface, since the shearing force that acts on the bonded interface during pipe expansion is alleviated further, the effect that the formation of cracks at the bonded interface is restrained is provided even in the case where pipe expansion of a high pipe expansion rate is performed.

Also, with the pipe expansion expanding method of metal-pipe bonded body by this invention, since a expandable metal-pipe bonded body, with which at least part of the bonded interface is inclined with respect to the radial direction of the metal pipes, is used and since the pipe expansion tool is moved from one metal pipe, with which the inclined part of the bonded interface is formed to have a protruding shape, towards another metal pipe, with which the inclined part of the bonded interface is formed to have a recessed shape, the effect that the formation of cracks at the bonded interface is restrained is provided even in the case where pipe expansion of a high pipe expansion rate is performed.

With this invention, since in the case where a metal pipe bonded body, with which a plurality of metal pipes are liquid phase diffusion bonded via a bonded interface with a inclined part, is inspected by the ultrasonic flaw detection method, an ultrasonic wave is made perpendicularly incident on the inclined part and the reflection echo that has been reflected from the inclined part is detected, the effect of improved precision of detection of flaws that have occurred at the inclined part is provided.

Also in the case where the bonded interface furthermore has a perpendicular part, the effect of enabling inspection of flaws at the perpendicular part at high precision is provided by the making of an ultrasonic wave obliquely incident on the perpendicular part and detecting the reflection echo that has been reflected from the perpendicular part.

Furthermore, the effect of enabling the inner face offset to be measured at high precision is provided by the making of an ultrasonic wave perpendicularly incident on a pair of metal pipes that are made adjacent each other via the bonded interface, the measurement of the pipe thickness from the difference in the arrival times of the surface echo and the bottom face echo, and the separate measurement of the surface offset.

Also, the effect of enabling the crystalline structure in the vicinity of the bonded body part is determined by the making of an ultrasonic wave be transmitted in the direction of the interior of the metal pipe in the vicinity of the bonded interface and the measurement of the backward scattering intensity.

Furthermore, the effect of enabling inspection for the existence of a solidified phase at the inner face end part in a nondestructive manner is provided by the making of an ultrasonic wave obliquely incident towards the inner face end part of the metal pipe bonded body and the measurement of the position of the reflected wave that has been reflected by the inner face of the metal pipe bonded body.

What is claimed is:

1. A metal-pipe bonded body, comprising:
   a plurality of metal pipes diffusion bonded via a bond interface defined by end portions thereof;
   wherein a middle portion of said bond interface is inclined with respect to a radius of said metal-pipe bonded body, and outer and inner end portions of said bond interface extend parallel to the radius of said metal-pipe bonded body to define flat portions of said bond interface; and
   wherein the plurality of pipes of said metal-pipe bonded body have undergone a pipe expansion process after being diffusion bonded such that the inner and outer diameters are expanded relative to inner and outer diameters of the pipes prior to being diffusion bonded.

2. The metal-pipe bonded body according to claim 1, wherein an inside diameter of the end portions of first and second metal pipes is larger than an inside diameter of an intermediate portion of each of the first and second metal pipes, the intermediate portion being defined along the longitudinal axis of each of said first and second metal pipes between the end portions.

3. The metal-pipe bonded body according to claim 1, wherein an inside diameter of the end portions of first and second metal pipes is larger than an inside diameter of an intermediate portion of each of the first and second metal pipes, the intermediate portion being defined along the longitudinal axis of each of said first and second metal pipes between the end portions.

4. The metal-pipe bonded body according to claim 2, wherein said metal-pipe bonded body includes a plurality of pipes having expanded inner and outer diameters relative to the inner and outer diameters of the pipes prior to being diffusion bonded, said expanded inner and outer diameters being expanded by a pipe expansion tool having a tip angle selected with the incline of the bond interface as a factor in the determination thereof.

5. A metal-pipe bonded body, comprising:
   a plurality of metal pipes diffusion bonded via a bond interface defined by end parts thereof;
   wherein said bond interface is curved and inclined with respect to a radius of the metal-pipe bonded body;
   wherein the plurality of pipes of said metal-pipe bonded body have undergone a pipe expansion process after being diffusion bonded such that the inner and outer diameters are expanded relative to inner and outer diameters of the pipes prior to being diffusion bonded.

* * * * *